United States Patent [19]

Herkes

[11] Patent Number: 4,885,391

[45] Date of Patent: Dec. 5, 1989

[54] PRODUCTION OF $C_4$ TO $C_{12}$ AMINES

[75] Inventor: Frank E. Herkes, La Place, La.

[73] Assignee: E. I. Du Pont De Nemours and Company, Wilmington, Del.

[21] Appl. No.: 143,834

[22] Filed: Jan. 14, 1988

[51] Int. Cl.$^4$ .............................................. C07C 85/12
[52] U.S. Cl. ..................................... 564/491; 564/461; 564/490
[58] Field of Search ........................ 564/461, 490, 491

[56] References Cited

U.S. PATENT DOCUMENTS

| 2,402,626 | 6/1946 | Howk | 564/490 |
|---|---|---|---|
| 3,544,485 | 12/1970 | Taira et al. | 564/491 |
| 4,140,720 | 2/1979 | Drake | 564/491 |
| 4,248,799 | 2/1981 | Drake | 564/491 |

FOREIGN PATENT DOCUMENTS 212986  4/1987  European Pat. Off. ............ 564/491

Primary Examiner—Glennon H. Hollrah
Assistant Examiner—Ba K. Trinh

[57] ABSTRACT

A process for the hydrogenation of $C_4$ to $C_{12}$ nitriles using a Raney cobalt catalyst promoted with chromium in which the catalyst activity is maintained by the addition of water. The process is particularly attractive to produce diamines by the hydrogenation of dinitriles.

5 Claims, No Drawings

PRODUCTION OF $C_4$ TO $C_{12}$ AMINES

FIELD OF THE INVENTION

This invention relates to the production of $C_4$ to $C_{12}$ amines by the hydrogenation of a $C_4$ to $C_{12}$ nitriles using a Raney cobalt catalyst containing chromium as a promoter. More particularly this invention relates to producing said amines in a more commercially, attractive manner by maintaining the reactivity of the catalyst by water addition.

BACKGROUND OF THE INVENTION

Processes for the hydrogenation of nitriles to produce amines using Raney cobalt catalyst containing chromium as a promoter are described in EPO patent application No. 0,212,986 assigned to W. R. Grace & Co. Among the nitriles mentioned are 2-methylglutaronitrile. This system employs an amine moderator which is soluble in the solvent employed to dissolve the nitrile.

Drake U.S. Pat. No. 4,248,799 discloses the hydrogenation of nitriles using Raney metal catalyst: nickel, and/or cobalt promoted with Group VIB metals, chromium, molybdenum and tungsten. The nitrile is contacted with hydrogen, ammonia, water and the catalyst.

SUMMARY OF THE INVENTION

The present invention is a process for preparing an amine having 4 to 12 carbon atoms by the hydrogenation of a nitrile having 4 to 12 carbon atoms using a Raney cobalt catalyst that is promoted with chromium, and in which the catalyst is kept active by the presence of 0.5 to 4% by weight, based on the nitrile, of water. The presence of this amount of water allows the hydrogenation reaction to proceed at a desirable rate for prolonged periods of time, at a temperature and pressure that allows the production of the desired amine product without substantial amounts of by-product. The process is carried out at a temperature of about 80° to 150° C. and at a pressure of about 400 to 2500 psig, preferably at a temperature of 90° to 130° C. and at a pressure of 600 to 1000 psig. The amine may be recovered from the reaction mixture by known methods, for example by distillation. The process is particularly suited for the preparation of diamines by hydrogenation of a dinitriles. Among the diamines that may be prepared by the process of this invention is 2-methyl,1,5-pentamethylenediamine by the hydrogenation of 2-methylglutaronitrile.

The process of this invention may be conducted by using the catalyst in a fixed bed, or in a slurry form. When employing the process using a fixed bed catalyst, the catalyst is in the form of granules having a particle size in the range of about 0.03 to 0.40 inch. When employing the process using a slurry catalyst, the catalyst is in finely divided form, preferably less than about 100 microns in size, for example about 60 to about 100 microns is satisfactory.

DETAILED DESCRIPTION OF THE INVENTION

The hydrogenation of nitriles having 4 to 12 carbon atoms for example 2-methylglutaronitrile to 2-methyl,1,5-pentamethylenediamine, is conducted at relatively low pressures in the presence of water, hydrogen, and a Raney cobalt catalyst promoted with chromium. Such catalysts are commercially available from W. R. Grace & Co., and contain about 0.5 to 6% by weight chromium. Such catalysts and the process for preparing them are disclosed in EPO application No. 0,212,986.

When the process of the invention is carried out using a fixed bed catalyst, the catalyst may be placed in an elongated verticle reactor, and the nitrile, hydrogen and water fed to the upper end of the reactor. The amine containing product may be removed from the lower end of the reactor, and the amine separated from the other components by distillation. In a large scale continuous system, it may be desirable to have present in the reactor a fluid that will serve as a heat sink, since the reaction is exothermic. A suitable fluid is a portion of the reaction product that has been cooled and is recycled. By using the cooled, recycled reaction product as the heat sink, it is unnecessary to carry out separation steps for the heat sink fluid; however, if desired other fluids could be used—, for example, solvents for the nitrile. The Grace EPO patent application No. 0,212,986 lists many suitable solvents that may be employed.

If the process of the invention is carried out using a slurry of catalyst, the finely divided catalyst is stirred, while it is in contact with the mixture containing the nitrile, hydrogen, and water.

EXAMPLES

Example I

A 300 cc Stainless Steel autoclave rated for 5000 psi at 343° C., was used for the example. Agitation at 1000 to 2500 rpms was accomplished using a Dispersimix turbine-type agitator containing a 1¼ inch impeller driven by an air motor. A sleeve-type jacketed furnace was used for heating the vessel. Temperature control and cooling were regulated by thermocouples and a flow transmitter, respectively. The vessel was equipped with a rupture disk venting into a catch pot, a valve for sample removal and pressure letdown, and a removable fitting for sample introduction. Pressure in the reactor was held constant by using a two stage pressure regulator in series with a 500 ml Stainless Steel reservoir containing a pressure gauge.

The vessel was charge with 4.02 grams of wet chromium promoted Raney cobalt catalyst powder (W. R. Grace) and 150 ml of 2-methylglutaronitrile (MGN) (99.7%). (The catalyst is shipped in water, and it was removed from the water but not dried). The catalyst had an average particle size of about 90 microns, and contained about 3% chromium. After sealing the vessel, hydrogen was added to 600 psi and maintained there through the use of 500 ml reservoir connected to a pressure gauge. Agitation of the mixture was kept constant at 2300 rpms. The rate (psi/min) of hydrogen uptake was calculated from an average of five slope measurements at approximately 50% MGN conversion. Continuous operation was accomplished by stopping the agitation when the hydrogen uptake was complete and removing a 100 ml product sample. After pressure let down, a fresh 100 ml sample of MGN was added and the above process repeated.

Initially the hydrogen uptake was 11.5 psi/min, but this rate of uptake diminished as the example continued. The amount of 2-methyl, 1,5-pentamethylenediamine (MPMD) produced was calculated on the basis of pounds per pound of catalyst. When 36.5 pounds of MPMD had been produced per pound of catalyst, the rate of hydrogen uptake had diminished to 5 psi/min. One percent by weight water was then introduced into the MGN feed, and by the time the amount of MPMD produced reached 41 pounds per pound of catalyst the rate of hydrogen uptake had increased to 10.5 psi/min. As the example continued the rate of hydrogen uptake diminished to 7.4 psi/min when the amount of MPMD per pound of catalyst reached 57. The amount of water in the feed was then increased to 2% by weight, and the hydrogen uptake increased to 8.6 psi/min.

Table I below contains additional data on this example.

TABLE I

| Sample No. | Lb MPMD/ Lb Cat. | % Water in Feed | Rate Hydrogen Uptake (psi/min) |
|---|---|---|---|
| 1  | 5.5  | 0 | 11.5 |
| 2  | 8.4  | 0 | 10   |
| 4  | 15.5 | 0 | 9.7  |
| 5  | 18   | 0 | 7.3  |
| 7  | 22.4 | 0 | 6.8  |
| 8  | 25   | 0 | 6.2  |
| 9  | 27   | 0 | 5.8  |
| 13 | 36.5 | 0 | 5.0  |
| 16 | 41   | 1 | 10.5 |
| 17 | 43.5 | 1 | 10.2 |
| 19 | 47.7 | 1 | 9.8  |
| 21 | 52.3 | 1 | 8.3  |
| 23 | 57   | 1 | 7.4  |
| 28 | 64.5 | 2 | 8.6  |

The addition of water increases the yield of MPMD and lowers the yield of the by-product, methylcyclopentanediamine (MCPD), and high boilers. A summary set forth in Table II below (an average of 5 analysis) shows the affect of water.

TABLE II

| Water % | Product Composition | | | | | | MGN % Conv. | MPMD % Yield |
| | MPMD % | 3MPIP* % | MGN % | MCPD % | HB** % | | | |
|---|---|---|---|---|---|---|---|---|
| 0 | 68.5 | 12.9 | 0.1 | 1.82 | 12.9 | 99 | 68.5 |
| 1 | 70.8 | 13.4 | 0.1 | 1.54 | 11.8 | 99 | 70.8 |
| 2 | 69.5 | 15.0 | 0.2 | 1.35 | 10.7 | 99 | 69.5 |

*3-methyl piperidine
**high boilers

Example 2

The reactor employed in this example is a seven foot long section of jacketed one inch carbon steel pipe, having a sintered metal gas/liquid distributor.

The reactor was loaded with 4.1 lbs of chromium promoted Raney cobalt catalyst having a particle size in the range of about 0.1 to 0.22 inch. The catalyst contained about 2.5% chromium. The reactor inlet temperatures were 110° C., and the pressure was 720 psig. The amount of water in the 2-methylglutaronitrile (MGN) feed stream was varied from 0.2 to 2% by weight.

The hydrogen, water and MGN were fed into the top of the reactor, and the reaction product removed at the bottom of the reactor.

The results are shown in Table III below:

TABLE III

| State | Fresh Feed Rate #/hr. | Water in Feed % | Product Composition | | | | | | MPMD #/hr | Prod. Rate Total MCPD** #/hr. |
| | | | MPMD % | 3MP* % | MCPD** % | AN*** % | MGN % | HB**** % | | |
|---|---|---|---|---|---|---|---|---|---|---|
| 1 | 0.6 | 0.2 | 65.7 | 19.8 | 3.26 | 0.3 | 0.5 | 10.7 | 0.42 | 0.021 |
| 2 | 0.6 | 2.0 | 64.9 | 20.3 | 3.52 | 0.1 | 0.2 | 9.1  | 0.42 | 0.023 |
| 3 | 1.0 | 0.2 | 46.2 | 7.1  | 1.28 | 18.3| 7.2 | 13.8 | 0.50 | 0.014 |
| 4 | 1.0 | 2.0 | 60.8 | 19.0 | 2.59 | 1.3 | 0.9 | 12.8 | 0.65 | 0.028 |

Comparison of states 1, 2, 3 and 4 show the acceleration of the hydrogenation with the addition of water as evidenced by reduced MGN and AN concentrations. Comparison of states 1,3, and 4 demonstrates the increased MPMD and MCPD production rates that can be achieved by the addition of 2% water.

Example 3

Isobutyronitrile Hydrogenation

The vessel used in Example 1 was charged with 125 g isobutyronitrile and 4.0 g chromium promoted Raney cobalt catalyst powder washed 4 times with tetrahydrofuran and isobutyronitrile to remove adsorbed water. The hydrogenation was performed at 600 psig pressure, 115° C. and 200 rpm stirring. Hydrogenation of isobutyronitrile containing 2% water in the feed yielded a hydrogen uptake rate of 52.8 psi/min resulting in a 81% yield of isopropylamine and 13% yield of the dimer, bis-(isopropyl)amine. Hydrogenation without water in the feed gave a hydrogen uptake rate of 28.9 psi/min. The yield of isopropylamine and dimer in the latter case was 86% and 8% respectively.

Example 4

Dicyanocyclooctane Hydrogenation

The vessel used in Example 1 was charged with 100 g dicyanocyclooctane (mixed isomers) and 6.0 g chromium promoted Raney cobalt powder catalyst washed 4 times with tetrahydrofuran to remove the adsorbed water. The hydrogenation was performed at 600 psig, 125° C., and 2000 rpm stirring. Addition of 2% water to the nitrile feed produced a hydrogen uptake rate of 19 psi/min resulting in a 91% yield of diaminomethylenecyclooctane. Six isomers (positional and geometrical) were detected by capillary gas chromatographic analysis. In the absence of water, the hydrogen uptake rate was only 9 psi/min. A 95% yield of diaminomethylenecyclooctane was observed.

This compound is useful as a curing agent for epoxy compounds.

I claim:

1. A hydrogenation process for the conversion of 2-methylglutaronitrile to the corresponding amine which comprises reacting a mixture consisting of 2-methylglutaronitrile, 0.5 to 4% by weight water, and hydrogen, by contacting said mixture with a catalyst of Raney cobalt containing chromium as a promoter, at a temperature of about 80° to 150° C. and at a pressure of about 400 to 2500 psig, and recovering the amine.

2. The process of claim 1 in which the mixture and hydrogen are fed downwardly through a fixed bed chromium promoted Raney cobalt catalyst.

3. The process of claim 1 in which the catalyst is finely divided and has a particle size less than about 100 microns and the catalyst is dispersed in the mixture 4. The process of claim 2 in which the Raney cobalt catalyst contains about 0.5 to 6% by weight chromium, and the catalyst is in the form of granules having a particle size of 0.03 to 0.40 inch.

5. The process of claim 4 in which the temperature is in the range of 90° to 130° C., and the pressure is in the range of 600 to 1000 psig.

* * * * *